United States Patent [19]

Rose et al.

[11] Patent Number: 5,378,369

[45] Date of Patent: Jan. 3, 1995

[54] SOLVENT EXTRACTION

[75] Inventors: Peter D. Rose; Trevor D. Phillips, both of Grahamstown; Ronald D. Sanderson, Stellenbosch, all of South Africa

[73] Assignee: Sasol Chemical Industries (Proprietary) Limited, Johannesburg, South Africa

[21] Appl. No.: 191,323

[22] Filed: Feb. 2, 1994

[30] Foreign Application Priority Data

Feb. 11, 1993 [ZA] South Africa ............ 93/0953

[51] Int. Cl.⁶ ............................................. B01D 61/16
[52] U.S. Cl. .................................. 210/637; 210/639; 210/651; 210/653
[58] Field of Search ............... 210/637, 639, 650, 651, 210/652, 653, 195.2

[56] References Cited

U.S. PATENT DOCUMENTS

| | | | |
|---|---|---|---|
| 4,320,050 | 3/1982 | Rebeller | 260/112 R |
| 4,680,314 | 7/1987 | Nonomura | 514/725 |
| 4,851,339 | 7/1989 | Hills | 435/67 |
| 5,110,475 | 5/1992 | Rossling | 210/640 |
| 5,157,132 | 10/1992 | Tan et al. | 549/413 |
| 5,245,095 | 9/1993 | Graves | 585/351 |
| 5,250,182 | 10/1993 | Bento | 210/641 |
| 5,279,847 | 1/1994 | Okonogi et al. | 426/603 |

FOREIGN PATENT DOCUMENTS

| | | |
|---|---|---|
| 1059716 | of 0000 | China . |
| 0037836 | 10/1981 | European Pat. Off. . |
| 0052777 | 6/1982 | European Pat. Off. . |
| 0053635 | 6/1982 | European Pat. Off. . |
| 00536635 | 6/1982 | European Pat. Off. . |
| 0258884 | 3/1988 | European Pat. Off. . |
| 0259109 | 3/1988 | European Pat. Off. . |
| 61109764 | of 0000 | Japan . |
| 87/03503 | 6/1987 | WIPO . |

OTHER PUBLICATIONS

Qiulin W. "Membrane Phase . . . ", Proceedings of the 1987 International Congress on Membranes and Membrane Processes (Jun. 1987), pp. 803–804.
Sullivan, D. E. "Structure of a Simple . . . ", J. Chem. Phys. 69(12) 15 Dec. 1978, pp. 5450–5457.
Chemical Abstracts, vol. 117, No. 9, Aug. 31, 1992, Columbus, Ohio, US 087053, Teng, J. et al., "Method for extracting . . . ".
Database WPI, Section Ch, Week 8628, Derwent Publications Ltd., London, G.B. Cl. A97, AN86–1783.
Brouwer et al., "Particle Interactions . . . ", Journal of Colloid and Interface Science, vol. 92, No. 1, Mar. 1983, p. 57.
Ftzler, F. "A Statistical Thermodynamic Model . . . ", Journal of Colloid and Interface Science, vol. 91, No. 1, Mar. 1983, pp. 43–45.
Aronson, et al., "On the Stability of Aqueous Films . . . ", Journal of Colloid and Interface Science, vol. 65, No. 2, Jun. 1978, pp. 296–306.
Toxvaerd, S. "Molecular dynamics Calculation . . . ", J. Chem. Phys. vol. 67, No. 11, Dec. 1, 1977, pp. 5291–5295.
Mitrovic et al. "Carrier Medicated Extraction . . . " Proceedings of the 3rd Chemical Engineering Conference, Italy, Yugoslavia, Austria, 1983, pp. 367 to 372.
Quingshan et al., Technology of Water Treatment, vol. 15, No. 2, Apr. 1989, pp. 101 to 104.
Lanba et al. Technology of Water Treatment, vol. 13, No. 4, Aug. 1987, pp. 240–243.
Gong Chengyuan et al., Technology of Water Treatment, vol. 18, No. 4, Aug. 1992, pp. 253–260.
Technology of Water Treatment, vol. 11, No. 4, Aug. 1987, pp. 8–11.
Shan et al, "The Measurement and Study . . . ", INET–R–67 pp. 56–65.
Povorov, A. A. et al. "Combined Utrafiltration . . . ", Abstract of 1993 Int'l Congress on Membranes–Membrane Processes (1993) p. 4.42.
Aurelle, Y. et al. "Ultrafiltration of Cutting 0.1 . . . ", Abstract of 1993 IntCongress on Membranes & Membrane Processes (1993) p. 4.24.
Ohtani et al, " Membrane Separation . . . ", Abstract of 1993 Int'l Congress on Membranes & Membrane Processes (1993) p. 1.33.
Nord, L. "Extraction Based on the Flow–Injection . . . ", Anal. Chim. Acta, 118, (1980) pp. 285–292.
Dialog File 653, Text of U.S. Pat 4680314.

*Primary Examiner*—Frank Spear
*Attorney, Agent, or Firm*—Ladas & Parry

[57] ABSTRACT

The invention provides a method for the solvent-extraction of β-carotene from an aqueous algal biomass suspension, whereby a vegetable oil which is immiscible with water is mixed with an aqueous biomass suspension, the biomass containing the β-carotene, to form a mixture of the organic phase and the aqueous suspension, whereby the β-carotene is caused to dissolve in the organic phase. This is followed by separation of the organic phase from the aqueous phase by passing the organic phase containing the dissolved β-carotene through a semi-permeable membrane to effect microfiltration or ultrafiltration of the organic phase. The membrane is of a material which is hydrophobic and the organic phase is passed through the membrane with a pressure drop across the membrane which is lower than that which causes the aqueous phase to pass through the membrane.

7 Claims, No Drawings

SOLVENT EXTRACTION

This invention relates to the solvent extraction of oil-soluble organic compounds from aqueous biomass suspensions. More particularly it relates to a method for the solvent extraction of an oil-soluble organic compound from an aqueous biomass suspension, suitable for extracting β-carotene from an aqueous algal biomass suspension.

According to the invention, in the solvent-extraction of β-carotene from an aqueous algal biomass suspension whereby an organic phase in the form of a vegetable oil which is immiscible with water is mixed with a suspension in an aqueous phase of an algal biomass, the biomass containing the β-carotene, to form a mixture the organic phase and the aqueous phase, whereby the β-carotene is caused to dissolve in the organic phase, followed by separation of the organic phase from the aqueous phase, there is provided the method whereby the separation is effected by passing the organic phase containing the dissolved β-carotene through a semipermeable membrane to effect microfiltration or ultrafiltration of the organic phase, the membrane being of a material which is hydrophobic and the organic phase being passed through the membrane with a pressure drop across the membrane which is lower than that which causes the aqueous phase to pass through the membrane.

By 'hydrophobic' is meant that the contact angle exhibited by a droplet of water on a surface provided by the material of the membrane is >90°, and the contact angle is preferably as high as practicable for the purpose of the method of the present invention, bearing in mind practical and economic considerations.

The aqueous algal biomass suspension may be of halophilic algae of the genus Dunaliella. Conveniently the algae may be of the species *Dunaliella salina* and the variety *bardawil*. Examples of other halophilic species of Dunaliella are *Dunaliella parva, Dunaliella tertiolecta, Dunaliella primolecta, Dunaliella peircei*, etc. All of these are well known but the presently preferred are high-β-carotene-producing strains of the species *Dunaliella salina*. *Dunaliella salina* is particularly suitable for producing β-carotene by the process according to the invention from saline solutions.

The biomass suspension may be relatively concentrated, the concentration of biomass solids in the suspension, on a dry basis, being at least 0,1 g/l, preferably 0,5–100 g/l, typically 5–20 g/l, eg 10 g/l. The concentration of β-carotene in the suspension may be 0,1–12% by mass of the solids, on a dry basis, usually 1–10%. eg 2%.

The aqueous algal biomass suspension may comprise aqueous algal biomass suspended in a saline solution, of the type used to culture the algal biomass. Numerous such solutions are known in the art, an example being that of Ben-Amotz A. and Avron M., Plant Physiology, Vol. 72, 593–597, (1983).

Vegetable oils which can be used include soya-bean oil, peanut oil and, in particular, sunflower seed oil, although other vegetable oils with similar suitable physical properties may naturally be used instead.

From the aforegoing it follows that, in a particular embodiment of the invention, the vegetable oil may be an edible oil selected from soya-bean oil, pea-nut oil and sun-flower oil, the suspension being of biomass of halophilic algae of the genus Dunaliella selected from the species *Dunaliella parva, D. tertiolecta, D. primolecta, D. peircei, D. salina* and mixtures thereof, the aqueous phase being a saline culture solution in which the biomass is present on a dry basis at a concentration of 50–20 g/l and in which the β-carotene is present at a concentration of 1–10% by mass.

In accordance with the method, the organic phase is preferably thoroughly admixed with the aqueous phase, to form an emulsion with an organic phase droplet size which is as small as practicable, taking practical and economic considerations into account, the proportions of oil and water in the emulsion being optimized by routine experimentation. The suspension may be heated to an extraction temperature of up to 120° C., preferably 50°–80° C., eg 60° C., to enhance β-carotene solubility in the oil and to enhance lysis of algal cells in the emulsion, which lysis is typically achieved mechanically, eg by means of a French Press. The heating may take place before or after, but conveniently simultaneously with, the mixing to form the emulsion, and the emulsion may be kept at the extraction temperature for at least 3 mins, preferably at least 5 mins, eg 5–10 mins or more, for adequate solvent-extraction of the β-carotene to take place.

In other words, the mixing may be such as to form an emulsion in which the organic phase is discontinuous and the aqueous phase is continuous, the organic phase having an average droplet size of at most 1000 μm, preferably 100–400 μm, the organic phase:aqueous phase mass ratio being in the range 1:50–1:1, preferably 1:35–1:15, eg 1:25, and the method including keeping the emulsion at a temperature of 50°–80° C. for at least 5 minutes before the ultrafiltration takes place.

After the solvent-extraction is sufficiently complete, the microfiltration or ultrafiltration may be carried out, at a temperature of 20°–80° C., eg at said elevated extraction temperature which reduces the oil viscosity and facilitates the microfiltration or ultrafiltration, although the microfiltration or ultrafiltration can naturally be carried out after some cooling at a lower temperature, such as 25° C. The pressure drop across the membrane during the filtration may be 5–100 kPa, preferably 50–95 kPa, more preferably 80–95, eg 90 kPa, and may be at least 5 kPa below the pressure drop at which breakthrough across the membrane of the aqueous phase takes place, preferably at least 7 kPa, eg 10 kPa below said pressure drop. Thus, in particular, the ultrafiltration may be carried out with the mixture at a temperature of 50°–80° C., at a pressure drop across the membrane of 80–90 kPa, the pressure drop being at least 5 kPa below that which causes the aqueous phase to pass through the membrane.

The flux rate through the membrane of the oil at the pressure in question may be set at 5–30 l/m²/hr (LMH), preferably 15–25 LMH, and the porosity and the thickness of the membrane will be selected accordingly. Microfiltration covers pore sizes of 0,5–50 μm, usually 0,5–10 μm, and ultrafiltration covers pore sizes of 0,005–0,5 μm. The maximum pore size of the membrane in the present invention is preferably 1,0 μm, more preferably 0,1 μm, the membrane thickness being selected by routine experimentation to provide an acceptable flux rate at an acceptable pressure drop across the membrane.

Hydrophobic materials from which the membrane can be made include polysulphones, such as polyether sulphone, polyolefins, such as polypropylene, and polyfluorinated hydrocarbons, such as polytetrafluoroethylene and polyvinylidene fluoride, although membranes made of cellulose ester, polystyrene, polyvinyl butyral, chlorinated polyvinyl chloride, diphenylopropane polycarbonate, poly(methyl-methacrylate) or poly(m-phenylene isophthalamide) can in principle be used, to the extent that they are hydrophobic.

It follows that, in a particular embodiment of the invention, the membrane may be selected from polysulphone membranes and polypropylene membranes, having a pore size of at most 0,1 μm, the membrane being selected to provide, at the pressure drop at which the organic phase is passed through the membrane, a flux rate of the organic phase through the membrane of 30–40 $l/m^2/hr$.

If desired, the method may include, before the oil extraction, a saponification step, to saponify chlorophyll in the biomass solution, to reduce chlorophyll contamination of the organic phase. This saponification step may be effected in any suitable way known in the art, eg by using potassium hydroxide. After the separation, the extracted algal biomass may be washed, filtered and dried, to provide a protein-containing by-product. Thus, the biomass may comprise protein and chlorophyll, the method including, prior to the ultrafiltration, a saponification step whereby the chlorophyll in the biomass is saponified, and the method including, after separation of the organic phase from the aqueous phase, separation of the biomass from the aqueous phase, followed by washing the biomass with water and drying of the biomass to form a protein-containing by-product.

If desired, at least a proportion of the filtered organic phase may be recycled to the emulsion and mixed therewith, to increase the concentration of β-carotene dissolved therein, eg to as close as feasible to that of a saturated solution. Furthermore, while the method will typically be operated batchwise, it can in principle be operated on a continuous or semi-continuous basis, eg in an ultrafiltration unit employing cross-flow and/or employing a cascade. In particular, the method may be carried out on a continuous basis and, after the separation of the organic phase from the aqueous phase, a proportion of at least 10%, preferably 20–80%, eg 50%, by mass of the separated organic phase being recycled to the mixture of the organic phase and the aqueous phase, thereby to increase the concentration of the β-carotene dissolved in the organic phase in the mixture.

The invention extends also to a solution of β-carotene dissolved in a vegetable oil, whenever extracted in accordance with a method as described above.

The invention will now be described, by way of illustration, with reference to the following worked Example:

EXAMPLE

*Dunaliella salina* algae in the aqueous saline solution of Ben-Amotz and Avnon, *supra*, at a concentration of 10 g/l on a dry basis and containing 2% by mass β-carotene based on the dry mass of the solid was solvent-extracted using commercial grade sunflower seed oil. For the extraction the sunflower seed oil was intimately mixed with the algal suspension to form an emulsion at a temperature of 50°–80° C., ie 60° C.

After an extraction time of 5–10 min, ie 10 min, the emulsion was subjected to ultrafiltration, using a hydrophobic polypropylene membrane formed from 1 mm diameter hollow polypropylene fibres, having a cut-off, ie a maximum pore size, of 0,1 μm, so that it retained particles of >0,1 μm particle size. The temperature of the emulsion at which filtration took place was 25° C., and the filtration took place through a membrane having an area of $3,8 \times 10^{-2}$ $m^2$. The pressure drop across the membrane was in the range 80–90 kPa, and the membrane thickness was such that a flux rate of 25 LMH was achieved. Tests confirmed that water breakthrough took place from the emulsion at a pressure drop across the membrane of >90 kPa, ie 90–100 kPa.

The oil phase, containing the dissolved β-carotene therein, was obtained in a filtered state, ready for use or further concentration of refinement of the β-carotene, if desired. The substantially oil-free aqueous biomass solution, from which the oil had been filtered, was retained by the membrane, in the form of a by-product comprising a protein-containing aqueous suspension from which could be obtained a protein-rich concentrate, by washing, filtering and drying.

An advantage of the invention, particularly as described with reference to the Example, is that it provides a single step filtration, whereby the emulsion can be separated into sunflower seed oil containing dissolved β-carotene on the one hand, and a substantially oil-free aqueous biomass suspension phase on the other. Further filtration of the separated oil can thus be obviated. The process lends itself to continuous or at least semi-continuous operation, and the proportion of water in the algal biomass suspension is not critical, as both the solvent extraction using the sunflower seed oil and the separation by ultrafiltration can be carried out on relatively dilute suspensions of algal biomass, which can reduce the necessity for any concentration and drying steps required to be carried out on the biomass suspension before the extraction. The risk of oxidation of the β-carotene is reduced, no gravity phase separation of the vegetable oil is necessary, and the filtered oil is substantially free of debris. A further particular advantage of the invention is that pressure drops across the membrane can be employed which are relatively low.

We claim:

1. In the solvent-extraction of β-carotene from an aqueous algal biomass suspension whereby an organic phase in the form of a vegetable oil which is immiscible with water is mixed with a suspension in an aqueous phase of an algal biomass, the biomass containing the β-carotene, to form a mixture of the organic phase and the aqueous phase, whereby the β-carotene is caused to dissolve in the organic phase, followed by separation of the organic phase from the aqueous phase, the method whereby the separation is effected by passing the organic phase containing the dissolved β-carotene through a semi-permeable membrane to effect microfiltration or ultrafiltration of the organic phase, the membrane being of a material which is hydrophobic and the organic phase being passed through the membrane with a pressure drop across the membrane which is lower than that which causes the aqueous phase to pass through the membrane.

2. A method as claimed in claim 1, in which the vegetable oil is an edible oil selected from soya-bean oil, pea-nut oil and sun-flower oil, the suspension being of biomass of halophilic algae of the genus Dunaliella selected from the species *Dunaliella parva, D. tertiolecta, D. primolecta, D. peircei, D. salina* and mixtures thereof, the aqueous phase being a saline culture solution in which the biomass is present on a dry basis at a concentration of 50–20 g/l and in which the β-carotene is present at a concentration of 1–10% by mass.

3. A method as claimed in claim 1, in which the mixing is such as to form an emulsion in which the organic phase is discontinuous and the aqueous phase is continuous, the organic phase having an average droplet size of 100–400 μm, the organic phase:aqueous phase mass ratio being in the range 1:50–1:1, and the method including keeping the emulsion at a temperature of 50°–80° C. for at least 5 minutes before the ultrafiltration takes place.

4. A method as claimed in claim 1, in which the ultrafiltration is carried out with the mixture at a temperature of 50°–80° C., at a pressure drop across the membrane of 80–90 kPa, the pressure drop being at least 5 kPa below that which causes the aqueous phase to pass through the membrane.

5. A method as claimed in claim 1, in which the membrane is selected from polysulphone membranes and polypropylene membranes, having a pore size of at most 0,1 μm, the membrane being selected to provide, at the pressure drop at which the organic phase is passed through the membrane, a flux rate of the organic phase through the membrane of 15–25 l/m$^2$/hr.

6. A method as claimed in claim 1, in which the biomass comprises protein and chlorophyll, the method including, prior to the ultrafiltration, a saponification step whereby the chlorophyll in the biomass is saponified, and the method including, after separation of the organic phase from the aqueous phase, separation of the biomass from the aqueous phase, followed by washing the biomass with water and drying of the biomass to form a protein-containing by-product.

7. A method as claimed in claim 1, in which the method is carried out on a continuous basis and, after the separation of the organic phase from the aqueous phase, a proportion of 20–80% by mass of the separated organic phase being recycled to the mixture of the organic phase and the aqueous phase, thereby to increase the concentration of the β-carotene dissolved in the organic phase in the mixture.

* * * * *